(12) United States Patent
Quintaine et al.

(10) Patent No.: US 11,479,740 B2
(45) Date of Patent: Oct. 25, 2022

(54) CYCLOHEXENE PROPANAL DERIVATIVES AS PERFUMING INGREDIENTS

(71) Applicant: FIRMENICH SA, Satigny (CH)

(72) Inventors: Julie Quintaine, Satigny (CH); Robert Moretti, Satigny (CH)

(73) Assignee: FIRMENICH SA, Satigny (CH)

( * ) Notice: Subject to any disclaimer, the term of this patent is extended or adjusted under 35 U.S.C. 154(b) by 129 days.

(21) Appl. No.: 16/954,260

(22) PCT Filed: Jun. 20, 2019

(86) PCT No.: PCT/EP2019/066362
§ 371 (c)(1),
(2) Date: Jun. 16, 2020

(87) PCT Pub. No.: WO2019/243506
PCT Pub. Date: Dec. 26, 2019

(65) Prior Publication Data
US 2022/0235290 A1    Jul. 28, 2022

(30) Foreign Application Priority Data
Jun. 21, 2018  (EP) .................................. 18178947

(51) Int. Cl.
| C11D 3/50 | (2006.01) |
| C11B 9/00 | (2006.01) |
| C07C 47/225 | (2006.01) |
| A61Q 13/00 | (2006.01) |
| D21H 17/06 | (2006.01) |
| A61K 8/33 | (2006.01) |

(52) U.S. Cl.
CPC .............. *C11B 9/0034* (2013.01); *A61K 8/33* (2013.01); *A61Q 13/00* (2013.01); *C07C 47/225* (2013.01); *C11D 3/50* (2013.01); *D21H 17/06* (2013.01); *C07C 2601/16* (2017.05)

(58) Field of Classification Search
CPC .......................... C07C 2601/16; C07C 47/225
See application file for complete search history.

(56) References Cited

U.S. PATENT DOCUMENTS

| 4,465,695 A | * | 8/1984 | Mookherjee | ............ | C07C 45/00 |
| | | | | | 426/538 |
| 4,480,647 A | * | 11/1984 | Sprecker | .................. | C07C 45/74 |
| | | | | | 131/276 |
| 4,487,701 A | * | 12/1984 | Sprecker | ............... | C07C 403/14 |
| | | | | | 510/106 |
| 4,492,645 A | * | 1/1985 | Sprecker | ............... | C07C 45/82 |
| | | | | | 512/4 |

| 2013/0090390 A1 | | 4/2013 | Singer et al. |
| 2018/0282660 A1 | * | 10/2018 | Moretti ................. C07C 47/225 |
| 2019/0225913 A1 | * | 7/2019 | Chapuis ............... C11D 3/2072 |

FOREIGN PATENT DOCUMENTS

| EP | 1054053 A2 | 11/2000 |
| EP | 2322495 A1 | 5/2011 |
| WO | 2017009175 A1 | 1/2017 |
| WO | 2017046071 A1 | 3/2017 |

OTHER PUBLICATIONS

International Search Report and Written Opinion for International Patent Application No. PCT/EP2019/066362, dated Sep. 20, 2019, 15 pages.
Skouroumounis et al.: "Synthesis of 1,3,4,5-Tetrahydro-2-benzoxepin Derivatives as Conformationally Restricted analogues of Cyclamenaldehyde-Type Compounds and as Intermediates for Highly Odour-Active Homologues", Helvetica Chimica Acta, vol. 79, No. 4, Jan. 1, 1996, pp. 1905-1109, XP009074278.
Dietrich et al.: "Amino resin microcapsules: I. Literatue and patent review", Acta Polymerica 40 (1989) Nr. 4, pp. 243-251.
Dietrich et al.: "Amino resin microcapsules: II. Preparation and morphology", Acta Polymerica 40 (1989) Nr. 5, pp. 325-331.
Dietrich et al.: "Amino resin microcapsules: III. Release properties", Acta Polymerica 40 (1989) Nr. 11, pp. 683-690.
Dietrich et al.: "Amino resin microcapsules: IIV. Surface tension of the resins and mechanism of capsule formation", Acta Polymerica 41 (1990) Nr. 2, pp. 91-95.
Lee et al.: "Microencapsulation of fragrant oil via in situ polymerization: effects of pH and melamineformaldehyde molar ratio", Journal of Microencapsulation, 2002 19:5, pp. 559-569.
Bône et al.: "Microencapsulated Fragrances in Melamine Formaldehyde Resins". CHIMIA 2011, 65, No. 3, pp. 177-181.

* cited by examiner

*Primary Examiner* — John R Hardee
(74) *Attorney, Agent, or Firm* — Armstrong Teasdale LLP

(57) ABSTRACT

Described herein is a compound of formula (I)

in the form of any one of its stereoisomers or a mixture thereof, and wherein $R^1$, $R^2$, $R^3$ and $R^4$ independently from each other, represent a hydrogen atom or a $C_{1-2}$ alkyl group. The use of compound of formula (I) as perfuming ingredients of floral type and the compounds as part of a perfuming composition or of a perfuming consumer product are also described.

12 Claims, No Drawings

CYCLOHEXENE PROPANAL DERIVATIVES AS PERFUMING INGREDIENTS

CROSS-REFERENCE TO RELATED APPLICATIONS

This application is a U.S. National Phase Application of International Patent Application No. PCT/EP2019/066362, filed Jun. 20, 2019, which claims the benefit of priority to European Patent Application No. 18178947.0, filed Jun. 21, 2018, the entire contents of each of which are hereby incorporated by reference herein.

TECHNICAL FIELD

The present invention relates to the field of perfumery. More particularly, the present invention relates to the use as perfuming ingredient of compounds of formula (I) as defined below, which are particularly useful perfuming ingredients of the floral type. Moreover, the present invention relates to a perfuming composition or a perfumed consumer product comprising the compounds of formula (I).

BACKGROUND

Some of the most sought ingredients in the perfumery field are the ones imparting a floral impression and in particular a lily of the valley odor, particularly because this delicate floral odor does not survive even the mildest of extraction methods to yield an essential oil. Said note is very appreciated and used in a multitude of perfumed consumer products. For many decades, a lot of effort has been invested in finding compounds possessing this very complex white floral odor, especially since the use of Lilial® (2-methyl-3-[4-(2-methyl-2-propanyl)phenyl]propanal, trademark from Givaudan-Roure SA, Vernier, Suisse) representing one of the most valuable perfuming ingredients with a lily of the valley and watery connotation, has been limited due to various reasons.

There is a need to develop novel perfuming ingredients conferring a floral odor note being as close as possible to the natural odor of the lily of the valley blossom.

US 2013/0090390 reports as a compound imparting said olfactory properties 3-(4-isopropylcyclohex-1-en-1-yl)propanal. In particular, (R)-3-(4-isopropylcyclohex-1-en-1-yl)propanal imparts a lily of the valley, floral, sweet, watery, powdery and ozone-like note, whereas (S)-3-(4-isopropylcyclohex-1-en-1-yl)propanal confers a lily of the valley, fruity, green, watery and aldehydic-like note.

The present invention provides a novel perfumery ingredient imparting lily of the valley note, by using compounds of formula (I) which imparts a less aggressive odor than the prior art. The prior art document mentioned above does not disclose the compounds of formula (I) or the organoleptic properties of the compounds of formula (I).

SUMMARY OF THE INVENTION

The invention relates to compound of formula (I) which imparts an odor of floral type, in particular lily of the valley (also named muguet) which is much appreciated in perfumery.

A first object of the present invention is a compound of formula

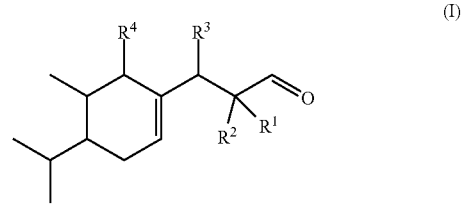

in the form of any one of its stereoisomers or a mixture thereof, and wherein $R^1$, $R^2$, $R^3$ and $R^4$ independently from each other, represent a hydrogen atom or a $C_{1-2}$ alkyl group.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is the use as a perfuming ingredient of a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I) or a composition as defined above.

DESCRIPTION OF THE INVENTION

Surprisingly, it has now been discovered that compounds of formula (I) possess a very interesting odor note with a lily of the valley connotation which is particularly appreciated. A first object of the present invention is a compound of formula

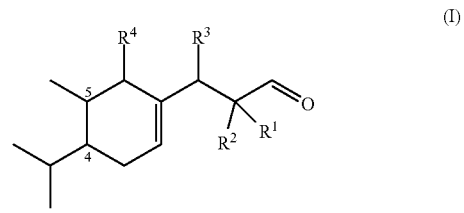

in the form of any one of its stereoisomers or a mixture thereof, and wherein $R^1$, $R^2$, $R^3$ and $R^4$ independently from each other, represent a hydrogen atom or a $C_{1-2}$ alkyl group. Said compounds can be used as perfuming ingredients, for instance to impart odor notes of the lily of the valley/cyclamen type with a green connotation.

For the sake of clarity, by the expression "any one of its stereoisomers or a mixture thereof", or the similar, it is meant the normal meaning understood by a person skilled in the art, i.e. that the invention compound can be a pure or be in the form of a mixture of enantiomers or diastereoisomers. According to any one of the above embodiments of the invention, the compound of formula (I) is in the form of a mixture of isomers comprising at least 55% of isomers with a R configuration on carbon 5 and at most 45% of isomers with a S configuration on carbon 5. Preferably, the compound of formula (I) is in the form of a mixture of isomers comprising at least 70% of isomers with a R configuration on carbon 5 and at most 30% of isomers with a S configuration on carbon 5. Even more preferably, the compound of formula (I) is in the form of a mixture of isomers comprising at least 80% of isomers with a R configuration on carbon 5 and at most 20% of isomers with a S configuration on carbon 5.

According to any one of the above embodiments of the invention, the compound of formula (I) is in the form of a mixture of isomers comprising at least 55% of isomers with a R configuration on carbon 4 and at most 45% of isomers with a S configuration on carbon 4. Preferably, the compound of formula (I) is in the form of a mixture of isomers comprising at least 70% of isomers with a R configuration on carbon 4 and at most 30% of isomers with a S configuration on carbon 4. Even more preferably, the compound of formula (I) is in the form of a mixture of isomers comprising at least 80% of isomers with a 4 configuration on carbon 5 and at most 20% of isomers with a 4 configuration on carbon 4.

Preferably, the compound of formula (I) is in the form of a mixture of isomers comprising at least 55% of isomers with a R configuration on carbon 4 and 5 and at most 45% of isomers with a S configuration on carbon 4 and 5. Preferably, the compound of formula (I) is in the form of a mixture of isomers comprising at least 70% of isomers with a R configuration on carbon 4 and 5 and at most 30% of isomers with a 4 and S configuration on carbon 5. Even more preferably, the compound of formula (I) is in the form of a mixture of isomers comprising at least 80% of isomers with a R configuration on carbon 4 and 5 and at most 20% of isomers with a S configuration on carbon 4 and 5. Even more preferably, the methyl substituent of carbon 5 and the isopropyl substituent of carbon 4 of the cyclohexenyl ring of the compound of formula (I) have a R configuration. In other words, the invention's compound is of formula

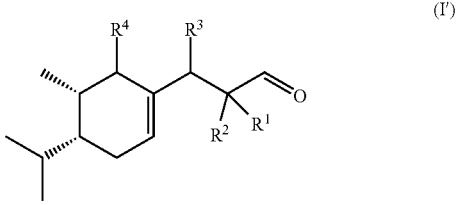

(I')

in the form of any one of its stereoisomers or a mixture thereof, and wherein $R^1$, $R^2$, $R^3$ and $R^4$ have the same meaning as defined above.

According to any one of the above embodiments of the invention, the compounds of formula (I) are $C_{13}$-$C_{19}$ compounds, preferably $C_{13}$-$C_{16}$ compounds, even more preferably $C_{13}$-$C_{14}$ compounds.

According to a preferred embodiment, the compound of formula (I) is in the form of any one of its stereoisomers or a mixture thereof, and wherein at least two groups among $R^1$, $R^2$, $R^3$ and $R^4$ independently from each other, represent a hydrogen atom and the other, independently from each other, represent a hydrogen atom or a $C_{1-2}$ alkyl group.

According to any one of the above embodiments of the invention, $R^2$ may be hydrogen atom or a methyl or ethyl group. Preferably, $R^2$ represents a hydrogen atom or a methyl group. Even more preferably, $R^2$ represents a hydrogen atom.

According to a preferred embodiment, the compound of the present invention is of formula

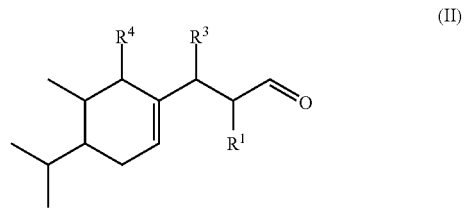

(II)

in the form of any one of its stereoisomers or a mixture thereof and wherein $R^1$, $R^4$ and $R^3$ independently from each other, represent a hydrogen atom or a $C_{1-2}$ alkyl group.

According to any one of the above embodiments of the invention, $R^3$ and/or $R^4$, independently from each other, may be a hydrogen atom or a methyl or ethyl group. Preferably, $R^3$ and/or $R^4$, independently from each other, represent a hydrogen atom or a methyl group. Typically, $R^3$ and/or $R^4$, independently from each other, represent a hydrogen atom or a methyl group and $R^1$ is a hydrogen atom or a $C_{1-2}$ alkyl group.

According to a specific embodiment, $R^1$ is hydrogen atom or a methyl or ethyl group and $R^3$ and/or $R^4$ represent a hydrogen atom or a methyl group.

Typically, $R^1$ and/or $R^3$ and/or $R^4$, independently from each other, represent a hydrogen atom or a methyl group.

Preferably, $R^3$ and/or $R^4$ represent a hydrogen atom. Typically, $R^3$ and/or $R^4$ represent a hydrogen atom and $R^1$ is a hydrogen atom or a $C_{1-2}$ alkyl group, preferably a hydrogen atom or a methyl group, more preferably a methyl group.

According to a preferred embodiment, the compound of the present invention is of formula

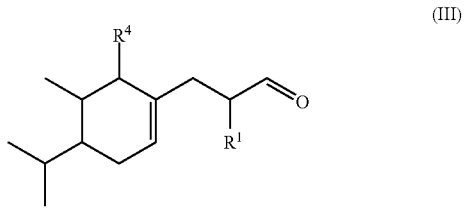

(III)

in the form of any one of its stereoisomers or a mixture thereof and wherein $R^1$ and $R^4$ independently from each other, represent a hydrogen atom or a $C_{1-2}$ alkyl group.

According to any one of the above embodiments of the invention, $R^4$ represents a hydrogen atom or a methyl group. Typically, $R^4$ represents a hydrogen atom or a methyl group and $R^1$ represents a hydrogen atom or a methyl or an ethyl group.

Preferably, $R^4$ represents a hydrogen atom. More preferably, $R^4$ represents a hydrogen atom and $R^1$ represents a hydrogen atom or a methyl or an ethyl group.

According to a preferred embodiment, the compound of the present invention is of formula

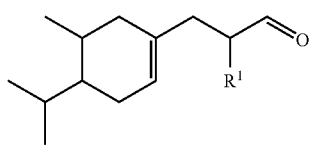

(IV)

in the form of any one of its stereoisomers or a mixture thereof and wherein $R^1$ represent a hydrogen atom or a $C_{1-2}$ alkyl group.

According to any one of the above embodiments of the invention, $R^1$ may be hydrogen atom or a methyl or an ethyl group. Preferably, $R^1$ may be a hydrogen atom or a methyl group. More preferably, $R^1$ represents a methyl group.

As specific examples of the invention's compound, one may cite, as non-limiting example, 3-((4-isopropyl-5-methylcyclohex-1-en-1-yl)-2-methylpropanal which provides a floral, lily of the valley, creamy and green organoleptic impression.

According to any one of the above embodiments of the invention, the compound of formula (I) may be selected from the group consisting of 3-((4-isopropyl-5-methylcyclohex-1-en-1-yl)-2-methylpropanal, 3-[(4R,5R)-4-isopropyl-5-methyl-1-cyclohexen-1-yl]-2-methylpropanal, 3-(4-isopropyl-5-methylcyclohex-1-en-1-yl) propanal, 3-[(4R,5R)-4-isopropyl-5-methyl-1-cyclohexen-1-yl]-2-ethylpropanal, 3-((4R,5R)-4-isopropyl-5-methyl-1-cyclohexen-1-yl)propanal, 3-[(4R,5R)-4-isopropyl-5-methyl-1-cyclohexen-1-yl]-2,2-dimethylpropanal and 3-((4R,5S,6R)-4-isopropyl-5,6-dimethylcyclohex-1-en-1-yl)-2-methylpropanal. Preferably, the compound of formula (I) may be 3-[(4R,5R)-4-isopropyl-5-methyl-1-cyclohexen-1-yl]-2-methylpropanal.

When the odor of the invention's compounds is compared with that of the prior art compound (R)-3-(4-isopropylcyclohex-1-en-1-yl)propanal, then the invention's compounds distinguish themselves by a clearly more floral, lily of the valley, creamy and green organoleptic sensation and by lacking the classic-aldehydic character of the prior art. The odor of the invention's compounds is also finer and devoid of the soapy/fatty side of aldehyde so characteristic of the prior art compound. The invention's compound provides a nicer organoleptic impression than the prior art which confers a more technical aspect; i.e. detergent and clean aldehyde. Said differences lend the invention's compounds and the prior art compounds to be each suitable for different uses, i.e. to impart different organoleptic impressions.

It has been discovered that the compound of formula (I) can be produced in an advantageous manner by means of alpha alkylation of an aldehyde with a strained polycyclic olefin followed by a ring opening step. Said process allows avoiding the formation of ketone side product.

Another object of the present invention is a process for the preparation of a compound of formula

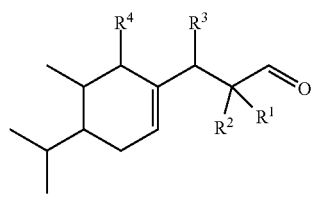

(I)

in the form of any one of its stereoisomers or a mixture thereof, and wherein $R^1$, $R^2$, $R^3$ and $R^4$ independently from each other, represent a hydrogen atom or a $C_{1-2}$ alkyl group comprising the step of an alpha alkylation of an aldehyde of formula, $R^2$—$CHR^1$—CHO wherein $R^1$ and $R^2$ has the same meaning as above with an olefin compound being a fused or bridged bicyclic or tricyclic compound with a olefin group in alpha of a ring junction; said step being performed in the presence of a photoredox catalyst, a hydrogen atom transfer donor, a secondary amine and light. Optionally, said process comprises a purification step, for example a column chromatography may be used typically a column chromatography on silica gel.

Said alkylation is followed by a ring opening.

By the term "secondary amine", it is meant the normal meaning in the art, i.e. the nitrogen atom is substituted by one hydrogen atoms and two groups different than hydrogen atom.

For the sake of clarity, by the term "photoredox catalyst", it is meant the normal meaning in the art, i.e. a catalyst absorbing light to accelerate a chemical reaction by activating of organic substrates via a single electron transfer process.

For the sake of clarity, by the expression "hydrogen atom transfer donor", it is meant the normal meaning in the art, i.e. a compound able to provide a hydrogen free radical. Hydrogen atom transfer is also called HAT.

According to any one of the above embodiments, the olefin may be a compound of formula

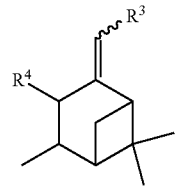

(V)

wherein $R^3$ and $R^4$ have the same meaning as above.

According to any embodiments of the invention, and independently of the specific aspects, the compound (I), as well as the compound (V), can be in the form of a racemate or in a form of any one of its stereoisomers or mixture thereof. For the sake of clarity by the term stereoisomer it is intended any diastereomer or enantiomer.

Indeed, the compound (I) or (V) may have several stereogenic centers which can have different stereochemistry (i.e. when two stereogenic centers are present, compound (I) or (V) can have (R,R) or (R,S) configuration). Each of said stereogenic centers can be in a relative or absolute configuration R or S or a mixture thereof or in other words said compound of formula (I) or (V) can be in a form of pure enantiomer or distereoisomer, or in a form of a mixture of stereoisomers.

According to any one of the above embodiments, the olefin can be added into the reaction medium of the invention's process in a large range of concentrations. As non-limiting examples, one can cite as olefin concentration values those ranging from about 1 mole equivalent to about 8 mole equivalents, relative to the amount of the aldehyde, preferably from about 1.2 mole equivalents to about 6 mole equivalents, relative to the amount of the aldehyde, 1.8 mole equivalents to about 3.5 mole equivalents, relative to the amount of the aldehyde. The optimum concentration of the olefin will depend, as the person skilled in the art knows, on the nature of the latter, on the nature of the aldehyde, the hydrogen atom transfer donor, the photoredox catalyst and/or the secondary amine, on the reaction temperature as well as on the desired time of reaction.

According to any one of the above embodiments, the photoredox catalyst may be an organic photocatalyst, or an iridium or a ruthenium complex, preferably, an iridium complex.

According to any one of the above embodiments, the photoredox catalyst may have a redox potential of at least 0.8V vs. SCE.

According to a particular embodiment, non-limiting examples of suitable photoredox catalyst may include [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (corresponding to Ir(dF(CF3)ppy)$_2$(dtbbpy)PF$_6$), [4,4'-Bis(1,1-dimethylethyl)-2,2'-bipyridine-κN1,κN1']bis[3,5-difluoro-2-[5-(methyl)-2-pyridinyl-κN]phenyl-κC]Iridium$^{(III)}$ hexafluorophosphate (corresponding to Ir(dF(Me)ppy)$_2$(dtbbpy)PF$_6$), [4,4'-Bis(1,1-dimethylethyl)-2,2'-bipyridine-κN1,κN1']bis[3,5-difluoro-2-[2-pyridinyl-κN]phenyl-κC]Iridium$^{(III)}$ hexafluorophosphate (corresponding to Ir(dFppy)$_2$(dtbbpy)PF$_6$) or [4,4'-Bis(1,1-dimethylethyl)-2,2'-bipyridine-κN1,κN1']bis[3-fluoro-5-trifluoromethyl-2-[5-(trifluoromethyl)-2-pyridinyl-κN]phenyl-κC]Iridium$^{(III)}$ hexafluorophosphate (corresponding to Ir(FCF$_3$(CF$_3$)ppy)$_2$(dtbbpy)PF$_6$). Preferably, the photoredox catalyst may be [4,4'-Bis(1,1-dimethylethyl)-2,2'-bipyridine-κN1,κN1']bis[3,5-difluoro-2-[5-(trifluoromethyl)-2-pyridinyl-κN]phenyl-κC]Iridium$^{(III)}$ hexafluorophosphate.

According to any one of the above embodiments, the photoredox catalyst can be added into the reaction medium of the invention's process in a large range of concentrations. As non-limiting examples, one can cite as photoredox catalyst concentration values those ranging from about 0.01 mol % to about 10 mol %, relative to the amount of the aldehyde, preferably from about 0.05 mol % to about 5 mol %, relative to the amount of the aldehyde, even more preferably, from about 0.1 mol % to about 1 mol %, relative to the amount of the aldehyde. The optimum concentration of the catalyst will depend, as the person skilled in the art knows, on the nature of the latter, on the nature of the aldehyde, the olefin, the hydrogen atom transfer donor and/or the secondary amine, on the reaction temperature as well as on the desired time of reaction.

According to any one of the above embodiments, the hydrogen atom transfer donor may be any hydrogen atom transfer donor used in radical chemistry such as metal hydride compounds such as tin, silicon, sulfur, selenium, boron or phosphorous derivatives or organic compounds such as malonitrile.

According to a particular embodiment, the hydrogen atom transfer donor is a sulfur derivative. Preferably, the hydrogen atom transfer donor is a thiophenol of formula

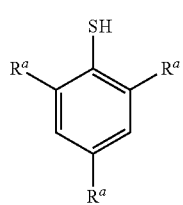

(VI)

wherein each R$^a$ represents, independently from each other, a hydrogen atom, a halogen atom, a C$_{1-2}$ linear alkyl group, a C$_{3-4}$ linear or branched alkyl group, a phenyl group optionally substituted by one to five halogen atoms and/or C$_{1-4}$ alkyl or alkoxyl groups or a silyl group trisubstituted with C$_{1-4}$ alkyl groups or an aryl groups; provided that at most two R$^a$ group represent an hydrogen atom. Preferably, the thiophenol may be selected from the group consisting of 2,4,6-trimethylbenzenethiol, 2,4,6-tri-iso-propylbenzenethiol, 2,6-dimethylbenzenethiol, 2,6-di-tert-butyl-4-methylbenzenethiol, 2,6-diisopropylbenzenethiol, 2,4,6-tri-tert-butylbenzenethiol, 4-tert-butylbenzenethiol and 4-fluorobenzenethiol. Preferably, the thiophenol may be selected from the group consisting of 2,4,6-trimethylbenzenethiol, 2,4,6-tri-iso-propylbenzenethiol, 2,6-dimethylbenzenethiol, 2,4,6-tri-tert-butylbenzenethiol, 4-tert-butylbenzenethiol and 4-fluorobenzenethiol. Preferably, the thiophenol may be selected from the group consisting of 2,6-dimethylbenzenethiol, 2,4,6-trimethylbenzenethiol, 2,6-di-tert-butyl-4-methylbenzenethiol, 2,6-diisopropylbenzenethiol, 2,4,6-tri-iso-propylbenzenthiol and 2,4,6-tri-tert-butylbenzenthiol Even more preferably, the thiophenol may be 2,4,6-tri-iso-propylbenzenethiol or 2,4,6-tri-tert-butyl-benzenthiol.

According to any one of the above embodiments, the thiophenol can be added into the reaction medium of the invention's process in a large range of concentrations. As non-limiting examples, one can cite as thiophenol concentration values those ranging from about 0.5 mol % to about 20 mol %, relative to the amount of the aldehyde, preferably from about 1 mol % to about 10 mol %, relative to the amount of the aldehyde. The optimum concentration of the thiophenol will depend, as the person skilled in the art knows, on the nature of the latter, on the nature of the aldehyde, the olefin, the photoredox catalyst and/or the secondary amine, on the reaction temperature as well as on the desired time of reaction.

According to any one of the above embodiments, the secondary amine may be a cyclic or acyclic amine optionally substituted by one to three halogen atoms or an acid or ester group. Preferably the secondary amine may be of formula

(VII)

wherein R$^b$ and R$^c$ represent, when taken separately, independently from each other, a C$_{1-4}$ alkyl group optionally substituted by one to three halogen atoms; or R$^b$ and R$^c$ represent, when taken together, a C$_{24}$ linear alkanediyl group optionally substituted by an ester or an acid group. Said secondary amine may be in the form of ammonium salt. Preferably, the secondary amine may be selected from the group consisting of 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, 2,2,2-trifluoro-N-ethylethan-1-amine, 2,2,2-trifluoro-N-ethylethan-1-aminium chloride, bis(2-chloroethyl)amine, bis(2-chloroethyl)aminium chloride, dimethyl amine and dimethylammonium chloride. Preferably, the secondary amine may be selected from the group consisting of 2-(bis(3,5-bis(trifluoromethyl)phenyl)((trimethylsilyl)oxy)methyl)pyrrolidine, 2,2,2-trifluoro-N-methylethan-1-amine, 2,2,2-trifluoro-N-methylethan-1-aminium chloride, bis(2-chloroethyl)amine, bis(2-chloroethyl)aminium chloride, dimethyl amine and dimethylammonium chloride. Even more preferably, the secondary amine may be 2,2,2-trifluoro-N-ethylethan-1-amine or 2,2,2-trifluoro-N-methylethan-1-amine. Even more preferably, the secondary amine may be 2,2,2-trifluoro-N-methylethan-1-amine. The secondary amine may be also in a form of a salt.

According to any one of the above embodiments, the secondary amine can be added into the reaction medium of the invention's process in a large range of concentrations. As non-limiting examples, one can cite as secondary amine concentration values those ranging from about 0.5 mol % to about 20 mol %, relative to the amount of the aldehyde, preferably from about 5 mol % to about 15 mol %, relative to the amount of the aldehyde. The optimum concentration of the secondary amine will depend, as the person skilled in the art knows, on the nature of the latter, on the nature of the aldehyde, the olefin, the photoredox catalyst and/or the hydrogen atom transfer donor, on the reaction temperature as well as on the desired time of reaction.

According to any one of the above embodiments, the light may have a wavelength comprised in the range between 250 nm and 800 nm. Preferably, the light may be UV visible light. Said light may be generated by LED lamp or LED strip.

According to any one of the above embodiments, the invention's process may optionally be carried out in the presence of an inorganic or organic acid such as hydrochloric acid, trifluoroacetic acid or para toluene sulfonic acid.

The reaction can be carried out in the presence or absence of a solvent. When a solvent is required or used for practical reasons, then any solvent current in such reaction type can be used for the purposes of the invention. Solvents with high dielectric constant are preferred. Non-limiting examples of solvents include DMSO, DMPU, DMF, DMA, NMP, acetonitrile, DME, methyl tetrahydrofuran or mixtures thereof. The choice of the solvent is function of the nature of the substrates and/or catalyst and the person skilled in the art is well able to select the solvent most suitable in each case to optimize the reaction.

The invention's process can be carried out at a temperature in the range comprised between 0° C. and 50° C., more. Preferably, the invention's process can be carried out at room temperature; i.e. around 25° C. Of course, a person skilled in the art is also able to select the preferred temperature according to the melting and boiling point of the starting and final products as well as the desired time of reaction or conversion.

The invention's process can be carried out under batch or continuous conditions.

Surprisingly, the invention's process allows avoiding the formation of the ketone side product also known as Kharasch ketone which is formed in a standard radical process. In other words, the invention's process provides a compound free of Kharasch ketone.

As mentioned above, the invention concerns the use as a perfuming ingredient of a compound of formula (I). In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but the addition of the invention's compound will impart to the final product its typical touch in the form of a note, touch or aspect depending on the dosage.

By "use of a compound of formula (I)" it has to be understood here also the use of any composition containing a compound of formula (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
Aldehydic ingredients: decanal, dodecanal, 2-methyl-undecanal, 10-undecenal, octanal and/or nonenal;
Aromatic-herbal ingredients: *eucalyptus* oil, camphor, eucalyptol, menthol and/or alpha-pinene;
Balsamic ingredients: coumarine, ethylvanillin and/or vanillin;
Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;
Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;
Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;
Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;
Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;
Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2, 2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3, 4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b] furan and any of its stereoisomers, heliotropin, anisic aldehyde, eugenol, cinnamic aldehyde, clove oil, 3-(1, 3-benzodioxol-5-yl)-2-methylpropanal and/or 3-(3-isopropyl-1-phenyl)butanal.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant", it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof. It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention. Similarly, according to another embodiment of the invention a perfuming composition comprises at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound of formula (I) is added. Consequently, another object of the present invention consists of a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactory effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.001% to 5% by weight, or even more, of the invention's compounds relative to the total weight of the consumer product into which they are incorporated.

The invention's compounds can be prepared according to different methods as described herein-below.

EXAMPLES

The invention will now be described in further detail by way of the following examples, wherein the abbreviations have the usual meaning in the art, the temperatures are indicated in degrees centigrade (° C.); NMR spectra were acquired using either a Bruker Advance II Ultrashield 400 plus operating at (400 MHz ($^1$H) and 100 MHz ($^{13}$C) or a Bruker Advance III 500 plus operating at (500 MHz ($^1$H) and 125 MHz ($^{13}$C) or a Bruker Advance III 600 cryoprobe operating at (600 MHz ($^1$H) and 150 MHz ($^{13}$C). Spectra were internally referenced and chemical shifts δ are indicated in ppm relative to TMS 0.0 ppm and coupling constants J are expressed in Hz.

Example 1

Preparation of 3-((4R,5R)-4-isopropyl-5-methylcyclohex-1-en-1-yl)-2-methylpropanal Step 1: (1S,4R,5S)-4,6,6-trimethylbicyclo[3.1.1]heptan-2-one The hydrogenation of (S)-(−)-Verbenone (100 g, 666 mmol) using Pd on activated carbon (5%, 1 g) under 40 bar of hydrogen gas was carried out within 15 hours at room temperature. The reaction mixture was filtered, rinsed with diethyl ether and concentrated. The crude product was purified by distillation (0.1 mbar, 70° C.) to afford (1S,4R,5S)-4,6,6-trimethylbicyclo[3.1.1]heptan-2-one as colorless oil (89.7 g, 589 mmol, 88% yield).

Step 2: (1S,2R,5R)-2,6,6-trimethyl-4-methylenebicyclo[3.1.1]heptane

Under argon, potassium 2-methylpropan-2-olate (132 g, 1.176 mol) was added portion wise to a solution of methyltriphenylphosphonium bromide (363 g, 1.016 mol) in dry THF (1 L). Then a solution of (1S,4R,5S)-4,6,6-trimethylbicyclo[3.1.1]heptan-2-one in dry THF (300 mL) was added dropwise. The mixture was stirred at room temperature for 15 hours and then poured over a saturated solution of ammonium chloride. The organic layer diluted in diethyl ether was washed with saturated solution of ammonium chloride and three times with brine. The concentrated organic phase was filtered to remove triphenylphosphine oxide. The solid was rinsed with pentane. After removal of solvent, the crude was distilled (25 mbar, 75° C.) to afford (1S,2R,5R)-2,6,6-trimethyl-4-methylenebicyclo[3.1.1]heptane as colorless oil (45.8 g, 0.305 mol, 52% yield).

$^{13}$C NMR (CDCl$_3$, 125 MHz): 152.4 (C), 105.8 (CH2), 52.3 (CH), 47.6 (CH), 40.1 (C), 33.6 (CH), 32.7 (CH2), 32.5 (CH2), 27.4 (CH3), 24.3 (CH3), 22.0 (CH3).

$^1$H NMR (CDCl$_3$, 500 MHz): 0.91 (s, 3H), 1.01-1.05 (m, 1H), 1.06 (d, J=7 Hz, 3H), 1.25 (s, 3H), 1.87 (td, J=2.2; 6 Hz, 1H), 2.14-2.21 (m, 2H), 2.43-2.48 (m, 2H), 2.77-2.85 (m, 1H), 4.60-4.62 (m, 2H).

Step 3: 3-((4R,5R)-4-isopropyl-5-methylcyclohex-1-en-1-yl)-2-methylpropanal

A glass tube with water jacket was charged with (1S,2R,5R)-2,6,6-trimethyl-4-methylenebicyclo[3.1.1]heptane (31 g, 206 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (0.17 g, 0.15 mmol), 2,4,6-tri-tert-butylbenzenethiol (0.96 g, 3.4 mmol), HCl (0.6 ml, 3.6 mmol), H$_2$O (3.7 ml, 205 mmol), DME (35 mL). Finally propionaldehyde (4 g, 68.9 mmol) and 2,2,2-trifluoro-N-methylethanamine (0.78 g, 6.9 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by distillation (0.03 mbar, 78° C.), then by column chromatography (heptane/EtOAc 495/5 as eluent) and then by preparative GC to afford the desired aldehyde as colorless oil (2.1 g, 10 mmol, 14% yield).

$^{13}$C NMR (CDCl$_3$, 125 MHz), mixture of two diastereoisomers (1:1): 205.41 (CH), 205.39 (CH), 131.73 (C), 123.18 (CH), 123.13 (CH), 44.39 (CH), 44.34 (CH), 43.57 (CH), 43.52 (CH), 39.21 (CH2), 38.89 (CH2), 37.04 (CH2), 36.94 (CH2), 30.18 (CH), 30.16 (CH), 27.25 (CH), 27.21 (CH), 26.42 (CH2), 26.41 (CH2), 21.23 (CH3), 20.77 (CH3), 20.76 (CH3), 13.23 (CH3), 12.30 (CH3), 12.26 (CH3).

$^1$H NMR (CDCl$_3$, 500 MHz), mixture of two diastereoisomers (1:1): 0.75 (d, J=6.9 Hz, 6H), 0.88 (d, J=6.5 Hz, 6H), 0.89 (d, J=6.5 Hz, 6H), 1.03 (d, J=1.9 Hz, 3H), 1.04 (d, J=1.9 Hz, 3H), 1.06-1.14 (m, 2H), 1.33-1.40 (m, 2H), 1.58-1.69 (m, 4H), 1.92-1.99 (m, 2H), 2.09-2.22 (m, 6H), 2.33-2.39 (m, 2H), 2.44-2.53 (m, 2H), 5.38-5.41 (m, 2H), 9.61 (d, J=1.9 Hz, 1H), 9.62 (d, J=2.2 Hz, 1H).

Example 2

Preparation of 3-(4-isopropyl-5-methylcyclohex-1-en-1-yl)propanal

Step 1: 4,6-Dimethylcyclohex-3-en-1-yl]ethanone

EtAlCl$_2$/hexanes (1 M solution; 68 ml; 68 mmol; 0.15 eq.) was added dropwise to a solution of pent-3-en-2-one (54.75 g at 70%; 456 mmol) in dry CH$_2$Cl$_2$ (400 ml), at −78° C. under N$_2$. The addition took 45 minutes. After 15 more minutes, isoprene (47.5 g; 684 mmol; 1.5 eq.) was added dropwise over 1 h. The reaction was then slowly warmed up overnight. In the morning, the internal temperature=15° C. The dark solution was cooled into an ice/water bath. 5% aq. HCl (500 ml) was added and the mixture was filtered through celite. Phases were separated. The organic phase was washed with aq. sat. NaHCO$_3$ and brine. Each aq. phase was reextracted twice with dichloromethane. Combined extracts were dried over sodium sulfate. The filtrate was concentrated on the rotavapor and the product directly distilled off the rotavapor (80° C./5 mbar) to give 4,6-Dimethylcyclohex-3-en-1-yl]ethanone as a colorless liquid (63.61 g; 94% pure; 393 mmol; 86%).

$^{13}$C-NMR: 213.2 (s); 133.6 (s); 118.7 (d); 54.4 (d); 38.2 (t); 30.6 (d); 29.3 (q); 28.4 (t); 23.3 (q); 19.8 (q).

$^1$H-NMR: 5.36 (m, 1H); 2.32 (m, 1H); 2.18-2.10 (m, 2H); 2.16 (s, 3H); 2.04-1.85 (m, 2 H); 1.71-1.65 (m, 1H); 1.65 (broad s; 3 H); 0.93 (d, J=7 Hz; 3 H).

Step 2: 4-Isopropenyl-1,5-dimethyl-cyclohexene

Solid t-BuOK (22.1 g; 193 mmol; 1.25 eq.) was added in one portion, under N$_2$ and without external cooling, to a slurry of methyltriphenylphosphonium bromide (73.2 g; 201 mmol; 1.3 eq) in dry THF (300 ml). After 1 h, the yellow reaction mixture was cooled into an ice/water bath. 4,6-Dimethylcyclohex-3-en-1-yl]ethanone (25 g; 154 mmol; 1 eq.) in dry THF (50 ml) was added dropwise. The reaction was warmed up to RT, then refluxed for 3 h. After recooling into an ice/water bath, water (500 ml) was added and the reaction was extracted with n-pentane (2×500 ml). Each organic phase was washed with 4:1 MeOH:H$_2$O (3×100 ml) and brine (300 ml). Combined extracts were dried over sodium sulfate. The product was purified by bulb-to-bulb distillation (60° C./4.4 mbar) to give 4-Isopropenyl-1,5-dimethyl-cyclohexene as a colorless liquid (22.3 g; 148 mmol; 96%). Diastereoisomeric ratio: 63:37.

$^{13}$C-NMR: 148.5 (s); 147.9 (s); 133.4 (s); 131.7 (s); 120.5 (d); 119.9 (d); 111.2 (t); 109.3 (t); 49.3 (d); 43.0 (d); 39.4 (t); 38.3 (t); 31.3 (t); 30.9 (d); 28.4 (d); 25.3 (T); 23.8 (q); 23.4 (q); 22.9 (q); 19.8 (q); 18.4 (q); 13.4 (q).

$^{1}$H-NMR: 5.37 (m, 1H); 4.82-4.65 (m, 2H); 2.31-1.83 (m, 4H); 1.77-1.54 (m, 8H); 0.84 (d, J=7 Hz; 1.8 H); 0.73 (d, J=7 Hz, 1.2 H).

Step 3: Ethyl 3-[4-isopropyl-5-methyl-cyclohexen-1-yl]propanoate

Solid MCPBA (36.6 g; 163 mmol; 1.1 eq.) was added portionwise (over 1 h) to 4-Isopropenyl-1,5-dimethyl-cyclohexene (22.3 g; 148 mmol) and NaHCO$_3$ (18.9 g; 223 mmol; 1.5 eq.) in dry CH$_2$Cl$_2$ (1 liter), under N$_2$ and ethanol/ice cooling (−5° C.). The reaction was slowly warmed up to RT overnight (reaction flask kept in the cooling bath). The solid was filtered off, rinsed with CH$_2$Cl$_2$. The filtrate was washed with 10% aq. NaHSO$_3$, aq. sat. NaHCO$_3$ and brine. Each aq. phase was extracted with CH$_2$Cl$_2$. Combined extracts were dried over sodium sulfate. The product was purified by bulb-to-bulb distillation (80° C./4.5 mbar) to give 1,3-dimethyl-4-(prop-1-en-2-yl)-7-oxabicyclo[4.1.0]heptane (21.84 g; 112 mol; 85% pure; 75%) as a colorless liquid (mixture of diastereoisomers). 11.05 g of this compound (56.5 mmol) were dissolved in ethyl acetate (50 ml) and hydrogenated at RT and AP in presence of 5% Pt—C (200 mg) until no more hydrogen is being consumed. The product was purified by bulb-to-bulb distillation (96° C./4.4 mbar) to give 4-isopropyl-1,3-dimethyl-7-oxabicyclo[4.1.0]heptane (10.17 g; 92% pure; 55.6 mmol; 98%) as a colorless liquid (mixture of diastereoisomers).

n-BuLi/1.6 M in hexanes (49 ml; 78 mmol; 1.4 eq.) was added dropwise (over 15 minutes) to a solution of diisopropylamine (8.5 g; 78 mmol; 1.5 eq.) in dry THF (100 ml) at −40° C. under N$_2$. After 10 more minutes at −40° C., the reaction was cooled at −78° C. 4-isopropyl-1,3-dimethyl-7-oxabicyclo[4.1.0]heptane (10.17 g; 92% pure; 55.6 mmol; 1 eq.) in dry THF (25 ml) is added dropwise (over 30 minutes). The cooling bath was removed and the reaction warmed up to RT, then to 50° C. for 1 h. After cooling into an ethanol/ice bath, aq. sat. NH$_4$Cl (100 ml) was added dropwise. The reaction was extracted twice with diethyl ether. Each organic phase was washed with brine. Combined extracts were dried over sodium sulfate. Bulb-to-bulb distillation (90° C./0.3 mbar) gave 5-isopropyl-4-methyl-2-methylenecyclohexan-1-ol (6.9 g; 87% pure; 36 mmol; 64%) as a colorless liquid. It was a mixture of 4 diastereoisomers. 3.1 g of 5-isopropyl-4-methyl-2-methylenecyclohexan-1-ol (16 mmol; 87% pure) were dissolved in toluene (100 ml). Triethylorthoacetate (5.42 g; 33 mmol; 2.1 eq.) and 2-ethylhexanoic acid (0.11 g; 0.8 mmol, 0.05 eq.) are added and the solution was heated in an oil bath over a 4 hours-period to 185° C. in a stainless steel autoclave (purged with nitrogen; magnetic stirring). The reaction was stirred to 185° C. for 24 h. The product was purified by bulb-to-bulb distillation (120° C./0.021 mbar) to give Ethyl 3-[4-isopropyl-5-methyl-cyclohexen-1-yl]propanoate (4.2 g; 89% pure; 15.7 mmol; 98%) as a colorless liquid (70:30 mixture of diastereoisomers).

$^{13}$C-NMR: 173.7 (s); 135.2 (s); 133.1 (s); 121.1 (d); 120.7 (d); 60.2 (t); 44.5 (d); 44.6 (d); 37.7 (t); 37.0 (t); 33.0 (t); 32.9 ( ); 32.8 (t); 32.5 (t); 30.7 (d); 30.2 (d); 27.2 (d); 26.9 (d); 26.4 (t); 24.0 (t); 21.3 (q); 21.2 ( ); 20.8 (q); 19.2 (q); 15.5 (q); 14.3 (q); 12.2 (q).

$^{1}$H-NMR: 5.39 (m, 0.6 H); 5.36 (m, 0.4 H); 4.12 (m, 2H); 2.41-2.36 (m, 2H); 2.27-2.22 (m, 2H); 2.15-2.07 (m, 1H); 1.99-1.89 (m, 2H); 1.81-1.54 (m, 2H); 1.39-1.08 (m, 2H); 1.25 (t, J=7 Hz, 3H); 0.93-0.87 (m, 6H); 0.77-0.73 (m, 3H).

Step 4:
3-(4-isopropyl-5-methylcyclohex-1-en-1-yl)propanal

Ethyl 3-[4-isopropyl-5-methyl-cyclohexen-1-yl]propanoate (4.2 g; 89% pure; 15.7 mmol) was dissolved in dry dichloromethane (100 ml) and the solution was cooled to −78° C. Diisobutylaluminum hydride (1 M in dichloromethane, 20 ml, 1.25 eq.) was added over 1 h. After 3 more hours at −78° C., the reaction was treated with 10% aq. Na/K-tartrate (Rochelle's salt; 70 g) and the mixture warmed up to RT and stirred overnight. Phases were separated. The aq. phase was extracted with dichloromethane. Each organic phase was washed with brine. Combined org. fractions were dried over anhydrous sodium sulfate. The product was purified by column chromatography on silica gel (eluent: heptane/ethyl acetate 15:1) followed by bulb-to-bulb distillation (100° C./0.7 mbar) to give 3-(4-isopropyl-5-methylcyclohex-1-en-1-yl)propanal (1.27 g; 93% pure; 6.5 mmol; 41%) as a colorless liquid. 2 diastereoisomers were obtained.

$^{13}$C-NMR: 202.9 (d); 202.8 (d); 134.8 (s); 133.3 (s); 121.5 (d); 121.1 (d): 44.5 (d); 43.6 (d); 41.9 (t); 41.8 (t); 37.9 (t); 37.2 (t); 30.7 (d); 30.2 (d); 30.1 (t); 29.7 (t); 27.2 (t); 26.8 (d); 26.3 (t): 24.1 (t); 21.3 (q); 21.2 (q); 20.8 (q); 19.2 (q); 15.5 (q); 12.2 (q).

$^{1}$H-NMR: 9.75 (m, 1H); 5.41-5.35 (m, 1H); 2.53-2.47 (m, 2H); 2.30-2.08 (m, 2H); 1.99-1.90 (m, 2H); 1.82-1.54 (m, 2H); 1.40-1.07 (m, 1H); 0.94-0.87 (m, 6H); 0.78-0.72 (m, 3H).

Example 3

Preparation of 3-((4R,5R)-4-isopropyl-5-methylcyclohex-1-en-1-yl)-2,2-dimethylpropanal Under nitrogen at room temperature, a solution of 3-((4R,5R)-4-isopropyl-5-methylcyclohex-1-en-1-yl)-2-methylpropanal (0.50 g, 2.4 mmol) in DMF (5 mL) was added dropwise over a solution of potassium tert-butoxide (0.40 g, 3.6 mmol, 1.5 eq) in DMF (5 mL). Then the reaction mixture was cooled down to 4° C. before the addition of iodomethane (1.02 g, 7.2 mmol, 3 eq).

The reaction mixture was poured over a saturated solution of ammonium chloride. Diethyl ether was added and the organic layer was washed with brine. The organic layer was dried over anhydrous sodium sulfate, filtrated and concentrated. The crude product was purified by column chromatography on silica gel (heptane/EtOAc 499/1) and then with bulb to bulb distillation to give the desired aldehyde as a colorless oil (0.21 g, 0.9 mmol, 39% yield).

$^{13}$C NMR (150 MHz, CDCl$_3$): 206.6 (CH), 131.3 (C), 125.0 (CH), 46.5 (C), 46.2 (CH2), 43.2 (CH), 39.0 (CH2), 30.1 (CH), 27.5 (CH), 26.5 (CH2), 22.1 (CH3), 21.6 (CH3), 21.2 (CH3), 20.7 (CH3), 12.2 (CH3).

$^1$H NMR (600 MHz, CDCl$_3$): 0.73 (d, J=7.0 Hz, 3H), 0.87 (d, J=6.6 Hz, 6H), 1.03 (s, 6H), 1.05-1.09 (m, 1H), 1.31-1.37 (m, 1H), 1.56-1.66 (m, 2H), 2.04-2.21 (m, 5H), 5.34-5.37 (m, 1H), 9.53 (s, 1H).

Example 4

Preparation of 2-(((4R,5R)-4-isopropyl-5-methylcyclohex-1-en-1-yl)methyl)butanal A glass tube with water jacket was charged with (1S,2R,5R)-2,6,6-trimethyl-4-methylenebicyclo[3.1.1]heptane (2.25 g, 15 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (5.6 mg, 0.005 mmol), 2,4,6-tri-tert-butylbenzenethiol (13.9 mg, 0.05 mmol), pTsOH (95.1 mg, 0.5 mmol), H$_2$O (0.27 ml, 15 mmol), DME (2.5 mL). Finally butyraldehyde (0.36 g, 5 mmol) and 2,2,2-trifluoro-N-methylethanamine (56.5 mg, 0.5 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by column chromatography (heptane/EtOAc 99/1 as eluent) and then by preparative GC to afford the desired aldehyde as colorless oil (0.218 g, 0.8 mmol, 17% yield).

$^{13}$C NMR (150 MHz, CDCl$_3$): 205.6 (CH), 132.0 (C), 122.9 (CH), 51.4 (CH), 43.5 (CH), 37.2 (CH2), 37.2 (CH2), 30.2 (CH), 27.2 (CH), 26.4 (CH2), 21.9 (CH2), 21.2 (CH3), 20.8 (CH3), 12.3 (CH3), 11.5 (CH3).

Example 5

Preparation of 3-((4R,5R)-4-isopropyl-5-methylcyclohex-1-en-1-yl)propanal

Step 1: 3-((4R,5R)-4-isopropyl-5-methylcyclohex-1-en-1-yl)propanenitrile (1S,2R,5R)-2,6,6-trimethyl-4-methylenebicyclo[3.1.1]heptane (4.01 g, 26.7 mmol), acetonitrile (57 mL, 1090 mmol, 40 eq) and tert-butylperoxide (0.79 g, 4 mmol, 0.2 eq) were charged in a stainless steel autoclave and the reaction mixture was heated at 150° C. overnight. The crude product was purified by column chromatography on silica gel (heptane/EtOAc as eluent) and then by bulb to bulb distillation (120° C. under 0.1 mbar) to afford 3-((4R,5R)-4-isopropyl-5-methylcyclohex-1-en-1-yl)propanenitrile as a colorless oil (1.05 g, 5.5 mmol, 21% yield).

$^{13}$C NMR (150 MHz, CDCl$_3$): 131.5 (C), 123.1 (CH), 119.7 (C), 43.4 (CH), 36.6 (CH2), 33.2 (CH2), 30.1 (CH), 27.1 (CH), 26.3 (CH2), 21.2 (CH3), 20.7 (CH3), 16.1 (CH2), 12.2 (CH3).

$^1$H NMR (600 MHz, CDCl$_3$): 0.76 (d, J=6.9 Hz, 3H), 0.88 (d, J=6.4 Hz, 3H), 0.89 (d, J=6.4 Hz, 3H), 1.10-1.15 (m, 1H), 1.34-1.40 (m, 1H), 1.62-1.69 (m, 2H), 2.11-2.31 (m, 5H), 2.40-2.44 (m, 2H), 5.47-5.50 (m, 1H).

Step 2: 3-((4R,5R)-4-isopropyl-5-methylcyclohex-1-en-1-yl)propanal

Under nitrogen, DIBAL (8 mL, 8 mmol) was added dropwise over a solution of 3-((4R,5R)-4-isopropyl-5-methylcyclohex-1-en-1-yl)propanenitrile (1.14 g, 5.5 mmol) in dichloromethane (16 mL) at −70° C. The reaction mixture was allowed to reach room temperature. Then the reaction mixture was added over ice, acidified with HCl 5% and washed with brine. The organic layer was dried over anhydrous magnesium sulfate and the solvent was evaporated. The crude product was purified by bulb to bulb distillation to give 3-((4R,5R)-4-isopropyl-5-methylcyclohex-1-en-1-yl)propanal as a colorless oil (0.36 g, 1.85 mmol, 34% yield).

$^{13}$C NMR (150 MHz, CDCl$_3$): 202.9 (CH), 133.2 (C), 121.1 (CH), 43.6 (CH), 41.9 (CH2), 37.2 (CH2), 30.2 (CH), 30.1 (CH2), 27.2 (CH), 26.3 (CH2), 21.2 (CH3), 20.8 (CH3), 12.2 (CH3).

$^1$H NMR (500 MHz, CDCl$_3$): 0.74 (d, J=7.0 Hz, 3H), 0.88 (d, J=6.7 Hz, 3H), 0.89 (d, J=6.7 Hz, 3H), 1.07-1.13 (m, 1H), 1.31-1.40 (m, 1H), 1.58-1.68 (m, 2H), 2.10-2.15 (m, 2H), 2.18-2.32 (m, 3H), 2.50 (td, J=1.8; 7.5 Hz, 2H), 5.37 (bs, 1H), 9.75 (t, J=1.9 Hz, 1H).

Example 6

Preparation of 3-((4R,5S,6R)-4-isopropyl-5,6-dimethylcyclohex-1-en-1-yl)-2-methylpropanal Step 1: (1S,3R,4S,5S)-3,4,6,6-tetramethylbicyclo[3.1.1]heptan-2-one Under nitrogen, butyl lithium (88 mL, 220 mmol, 1.3 eq) was added dropwise to a solution of diisopropylamine (31 mL, 221 mmol, 1.3 eq) in THF (130 mL) at −75° C. and the mixture was stirred for 20 min. Then a solution of (1S,4R,5S)-4,6,6-trimethylbicyclo[3.1.1]heptan-2-one (24.94 g, 164 mmol) in THF (70 mL) was added dropwise. Finally, iodomethane (14 mL, 224 mmol, 1.4 eq) was rapidly added. The reaction mixture was allowed to reach room temperature. The reaction mixture was poured over a saturated solution of ammonium chloride. Diethyl ether was added and the organic layer was washed with brine. The organic layer was dried over anhydrous sodium sulfate, filtrated and concentrated. The crude product was purified by distillation under vacuum (70° C. under 5 mbar) to afford (1S,3R,4S,5S)-3,4,6,6-tetramethylbicyclo[3.1.1]heptan-2-one as a colorless oil (23.4 g, 120 mmol, 73% yield).

$^{13}$C NMR (125 MHz, CDCl$_3$): 216.2 (C), 58.4 (CH), 47.9 (CH), 46.8 (CH), 41.2 (CH), 40.1 (C), 28.9 (CH2), 27.0 (CH3), 24.1 (CH3), 20.0 (CH3), 19.8 (CH3).

$^1$H NMR (500 MHz, CDCl$_3$): 1.02 (s, 3H), 1.18 (d, J=7.3 Hz, 3H), 1.29 (d, 1H), 1.30 (d, J=7.3 Hz, 3H), 1.34 (s, 3H), 1.83-1.90 (m, 1H), 2.10-2.19 (m, 2H), 2.58-2.63 (m, 2H).

Step 2: (1S,2R,3R,5S)-2,3,6,6-tetramethyl-4-methylenebicyclo[3.1.1]heptane

Under nitrogen, potassium 2-methylpropan-2-olate (15.0 g, 134 mol, 2 eq) was added portion wise to a solution of methyltriphenylphosphonium bromide (40.4 g, 113 mol, 1.6 eq) in dry THF (90 mL) at room temperature. Then a solution of (1S,3R,4S,5S)-3,4,6,6-tetramethylbicyclo[3.1.1]heptan-2-one in dry THF (40 mL) was added dropwise. The mixture was stirred at room temperature for 6 hours and then poured over a saturated solution of ammonium chloride. The organic layer diluted in diethyl ether was washed with saturated solution of ammonium chloride and three times with brine. The organic layer was dried over anhydrous sodium sulfate, filtrated and concentrated. Pentane (100 mL) was added to the concentrated organic phase in order to precipitate and remove by filtration triphenylphosphine oxide. The solid was rinsed with pentane. After removal of solvent, the crude was distilled (10 mbar, 130° C.) to afford (1S,2R,3R,5S)-2,3,6,6-tetramethyl-4-methylenebicyclo [3.1.1]heptane as colorless oil (8.1 g, 46 mmol, 67% yield).

$^{13}$C NMR (125 MHz, CDCl$_3$): 157.9 (C), 106.0 (CH2), 53.3 (CH), 48.1 (CH), 43.6 (CH), 39.9 (C), 37.9 (CH), 32.8 (CH2), 27.3 (CH3), 24.4 (CH3), 23.8 (CH3), 20.8 (CH3).

$^{1}$H NMR (500 MHz, CDCl$_3$): 0.90 (s, 3H), 0.94 (d, J=9.2 Hz, 1H), 1.07 (d, J=7.4 Hz, 3H), 1.22 (d, J=7.2 Hz, 3H), 1.25 (s, 3H), 1.62-1.68 (m, 1H), 1.86-1.89 (m, 1H), 2.26-2.33 (m, 1H), 2.40-2.49 (m, 2H), 4.67 (t, J=1.9 Hz, 1H), 4.72 (t, J=1.9 Hz, 1H).

Step 3: 3-((4R,5S,6R)-4-isopropyl-5,6-dimethylcyclohex-1-en-1-yl)-2-methylpropanal A glass tube with water jacket was charged with (1S,2R, 3R,5S)-2,3,6,6-tetramethyl-4-methylenebicyclo[3.1.1]heptane (5.42 g, 10.1 mmol), [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium$^{(III)}$ hexafluorophosphate (12.9 mg, 0.01 mmol), 2,4,6-tri-tert-butylbenzenethiol (69.5 mg, 0.25 mmol), HCl (0.83 mL, 6M solution, 0.5 mmol), H$_2$O (0.54 ml, 30 mmol), DME (5 mL). Finally propionaldehyde (0.59 g, 10 mmol) and 2,2,2-trifluoro-N-methylethanamine (128 mg, 1.1 mmol) were added. The mixture was stirred at RT and placed under Blue LED lamp for 24 h. The aqueous layer was taken off, diethylether was added and the organic phase was washed twice with water, dried over magnesium sulfate, and the solvent was evaporated. The crude product was purified by column chromatography (heptane/EtOAc 49/1 as eluent) and then by preparative GC to afford the desired aldehyde as colorless oil (0.10 g, 0.5 mmol, 15% yield).

$^{13}$C NMR (125 MHz, CDCl$_3$): 205.3 (CH), 136.5 (C), 123.1 (CH), 44.7 (CH), 39.3 (CH), 38.1 (CH), 35.9 (CH2), 34.3 (CH), 29.9 (CH), 26.9 (CH2), 21.3 (CH3), 20.7 (CH3), 20.0 (CH3), 13.3 (CH3), 12.8 (CH3).

$^{1}$H NMR (500 MHz, CDCl$_3$): 0.72 (d, J=9.4 Hz, 3H), 0.74 (d, J=9.4 Hz, 3H), 0.86-0.91 (m, 12H), 1.02-1.08 (m, 12H), 1.19-1.29 (m, 2H), 1.35-1.43 (m, 2H), 1.54-1.64 (m, 2H), 1.75-1.86 (m, 5H), 2.06-2.36 (m, 3H), 3.31-2.36 (m, 1H), 2.43-2.57 (m, 3H), 5.30 (m, 2H), 9.57 (d, J=2.6 Hz, 1H), 9.65 (d, J=1.4 Hz, 1H).

Example 7

Preparation of a Perfuming Composition

A perfuming composition for fabric softener, was prepared by admixing the following ingredients:

Parts by weight Ingredient
Benzyl acetate 600
Carbinol acetate 100
(Z)-3-hexen-1-ol acetate 20
Cinnamic alcohol 100
Anisic aldehyde 40
C 12 Aldehyde 10
Hexylcinnamic aldehyde 1400
Allyl amyl glycolate 40
Methyl anthranilate 20
Gamma undecalactone 100
Nitrile citronellyl 20
Verdyl acetate 200
Verdyl propionate 100
Damascone alpha 10
Dartanol®[1] 140
Dihydromyrcenol 400
Diphenyl oxide 100
Eugenol 100
Habanolide®[2] 1000
Hedione®[3] 1000
Phenethylol 1000
2,2,2-trichloro-1-phenylethyl acetate 40
Amyl salicylate 1200
Terpineol 1000
Verdox™[4] 200
Ylang essential oil 60
9000

1) (1'R,E)-2-ethyl-4-(2',2',3'-trimethyl-3'-cyclopenten-1'-yl)-2-buten-1-ol; origin: Firmenich SA, Geneva, Switzerland
2) Pentadecenolide; origin: Firmenich SA, Geneva, Switzerland
3) Methyl dihydrojasmonate; origin: Firmenich SA, Geneva, Switzerland
4) 2-tert-butyl-1-cyclohexyl acetate; origin: International Flavors & Fragrances, USA The addition of 1000 parts by weight of 3-((4R,5R)-4-isopropyl-5-methylcyclohex-1-en-1-yl)-2-methylpropanal to the above-described composition imparted to the latter a more floral, lily of the valley, creamy and green connotation.

When, instead of the invention's compound, the same amount of 3-((S)-4-isopropylcyclohex-1-en-1-yl)-2-methylpropanal was used, the composition acquired a distinctly fresh cyclamen and lily of the valley connotation and conferred more watery freshness to its top and bottom note.

When instead of the invention's compound, the same amount of (−)-(S)-3-(4-isopropylcyclohex-1-en-1-yl)propanal reported in US 2013/0090390, was used, the results was totally different as the composition acquired a distinctly clean aldehydic, citrus-lime and mandarine connotation which is classical in this kind of notes. Said compound imparted an aldehydic-citrus note instead of a floral note.

The invention claimed is:

1. A compound of formula

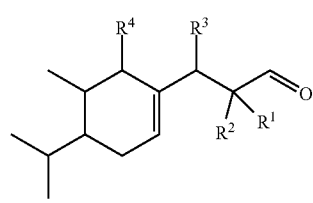

(I)

in the form of any one of its stereoisomers or a mixture thereof, and wherein R$^1$, R$^2$, R$^3$ and R$^4$ independently from each other, represent a hydrogen atom or a C$_{1-2}$ alkyl group.

2. The compound according to claim 1, wherein at least two groups among R$^1$, R$^2$, R$^3$ and R$^4$, independently from each other, represent a hydrogen atom and the other, independently from each other, represent a hydrogen atom or a C$_{1-2}$ alkyl group.

3. The compound according to claim 1, wherein R$^2$ is a hydrogen atom.

4. The compound according to claim 1, wherein the compound is of formula

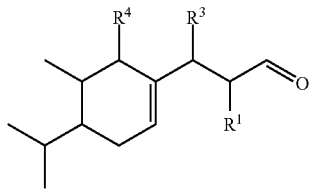

(II)

in the form of any one of its stereoisomers or a mixture thereof, and wherein $R^1$, $R^3$ and $R^4$ have the same meaning as defined in claim 1.

5. The compound according to claim 1, wherein $R^3$ and/or $R^4$ independently from each other is a hydrogen atom.

6. The compound according to claim 1, wherein the compound is of formula

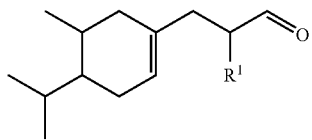

(IV)

in the form of any one of its stereoisomers or a mixture thereof and wherein $R^1$ has the same meaning as defined in claim 1.

7. The compound according to claim 1, wherein $R^1$ is a methyl group.

8. A method to confer, enhance, improve, or modify the odor properties of a perfuming composition or of a perfumed article, wherein the method comprises adding to said composition or article an effective amount of at least one compound of formula (I) as defined in claim 1.

9. A perfuming composition comprising:
   i) at least one compound of formula (I), as defined in claim 1;
   ii) at least one ingredient selected from the group consisting of a perfumery carrier and a perfumery base; and
   iii) optionally at least one perfumery adjuvant.

10. A perfumed consumer product comprising at least one compound of formula (I), as defined in claim 1.

11. The perfumed consumer product according to claim 10, wherein the perfumed consumer product is a perfume, a fabric care product, a body-care product, a cosmetic preparation, a skin-care product, an air care product, or a home care product.

12. The perfumed consumer product according to claim 11, wherein the perfumed consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product, or a car care product.

* * * * *